United States Patent [19]

Jäger et al.

[11] Patent Number: 4,505,922

[45] Date of Patent: Mar. 19, 1985

[54] TRIAZOLEALKYNOL FUNGICIDAL AGENTS

[75] Inventors: Gerhard Jäger, Leverkusen; Karl H. Büchel, Burscheid; Wolfgang Krämer, Wuppertal; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 385,354

[22] Filed: Jun. 7, 1982

[30] Foreign Application Priority Data

Jun. 23, 1981 [DE] Fed. Rep. of Germany ....... 3124580

[51] Int. Cl.³ .................. A01N 43/50; A01N 43/64; C07D 233/60; C07D 249/08
[52] U.S. Cl. .................. 514/383; 548/101; 548/262; 548/341; 514/399
[58] Field of Search ...... 548/101, 262, 341; 424/269, 245, 232, 273 R

[56] References Cited

U.S. PATENT DOCUMENTS

| | | | |
|---|---|---|---|
| 3,940,414 | 2/1976 | Kramer et al. | 548/341 |
| 3,952,002 | 4/1976 | Kramer et al. | 424/269 |
| 4,255,434 | 3/1981 | Kramer et al. | 424/269 |
| 4,414,210 | 11/1983 | Miller et al. | 548/262 |

FOREIGN PATENT DOCUMENTS

| | | |
|---|---|---|
| 0019153 | 11/1980 | European Pat. Off. . |
| 0021345 | 1/1981 | European Pat. Off. . |
| 0025516 | 3/1981 | European Pat. Off. . |
| 0052424 | 5/1982 | European Pat. Off. . |
| 2654890 | 12/1976 | Fed. Rep. of Germany ...... 548/262 |
| 1464224 | 2/1977 | United Kingdom ............... 548/262 |

OTHER PUBLICATIONS

Horsfall, "Fungicides and Their Action, " (Waltham, Mass., 1945), pp. 151-152.

*Primary Examiner*—Alton D. Rollins
*Attorney, Agent, or Firm*—Sprung Horn Kramer & Woods

[57] ABSTRACT

A fungicidal composition comprising a fungicidally effective amount of an alkinyl-azole derivative of the formula

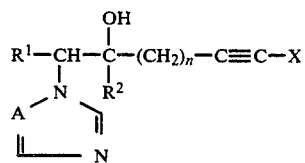

in which
A is a nitrogen atom or the CH group,
$R^1$ is an optionally substituted aryl or optionally substituted aryloxy group,
$R^2$ is an alkyl group which is optionally substituted by halogen, or an optionally substituted aryl group,
X is a hydrogen, bromine or iodine atom, and
n is 0 or 1 or an acid addition salt or metal salt complex thereof, in admixture with a diluent. Many of the compounds are new.

15 Claims, No Drawings

TRIAZOLEALKYNOL FUNGICIDAL AGENTS

The present invention relates to the use as fungicides, of certain alkinyl-azole derivatives, some of which are known.

It has already been disclosed that 1-phenoxy-1-triazolyl-alkanol derivatives have good fungicidal properties (see U.S. Pat. No. 3,952,002). However, the action of these compounds is not always completely satisfactory in some fields of indication, particularly when low amounts or concentrations are used.

It has now been found that certain alkinyl-azole derivatives, some of which are known, of the general formula

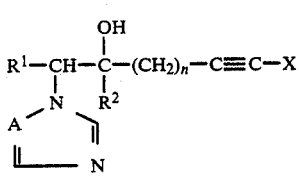

in which
A represents a nitrogen atom or the CH group,
$R^1$ represents an optionally substituted aryl or optionally substituted aryloxy group,
$R^2$ represents an alkyl group which is optionally substituted by halogen, or an optionally substituted aryl group,
X represents a hydrogen, bromine or iodine atom, and
n is 0 or 1,
and their acid addition salts and metal salt complexes have good fungicidal properties.

According to the present invention we provide a fungicidal composition, characterized in that it contains as active ingredient an alkinyl-azole derivative of formula (I), as defined above, or an acid addition salt or metal salt complex thereof, in admixture with a solid or liquefied gaseous diluent or carrier or in admixture with a liquid diluent or carrier containing a surface-active agent.

The present invention further relates to a method of combating fungi, characterized in that there is applied to the fungi, or to a habitat thereof, an active ingredient, as defined above, alone or in the form of a composition containing said active ingredient in admixture with a diluent or carrier.

The compounds of the formula (I) have two asymmetric carbon atoms; they can therefore be present as two geometrical isomers (threo-form and erythroform), which can be produced in varying proportions.

Surprisingly, the alkinyl-azole derivatives to be used according to the invention exhibit a better fungicidal activity than the 1-phenoxy-1-triazolyl-alkanol derivatives which are known from the state of the art and which are similar compounds in terms of their action. The use, according to the invention, of the largely new compounds of the formula (I) thus represents an enrichment of the art.

Formula (I) gives the general definition of the alkinyl-azole derivatives to be used as fungicides according to the present invention.

Preferred compounds for use according to the present invention are those of the general formula

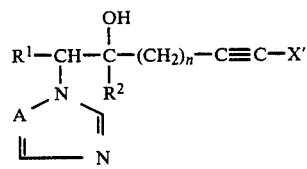

in which
$R^1$ represents an aryl or aryloxy group which is optionally monosubstituted or polysubstituted by identical or different substituents and has 6 to 10 carbon atoms (the following being preferred substituents: halogen, alkyl having 1 to 4 carbon atoms, alkoxy having 1 to 4 carbon atoms, nitro, halogenoalkyl having 1 or 2 carbon atoms and 1 to 5 identical or different halogen atoms, such as fluorine and chlorine, and phenyl which is optionally substituted by halogen);
$R^2$ represents a straight-chain or branched alkyl group having 1 to 4 carbon atoms, a tert-butyl group which is substituted by halogen, or an aryl group which is optionally monosubstituted or polysubstituted by identical or different substituents and has 6 to 10 carbon atoms (the preferred aryl substituents already mentioned under $R^1$ being preferred substituents in this instance also); $X'$ represents a bromine or iodine atom, or also represents a hydrogen atom when $R^1$ does not simultaneously represent an optionally substituted aryloxy group, $R^2$ does not simultaneously represent an alkyl group or an optionally substituted aryl group, and A does not simultaneously represent a nitrogen atom; and
A and n have the abovementioned meanings.

Compounds of the general formula

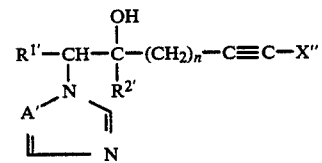

in which
$R^{1'}$ represents an aryloxy group which is optionally monosubstituted or polysubstituted by identical or different substituents and has 6 to 10 carbon atoms (the preferred aryl substituents already mentioned for $R^1$ in compounds of formula (Ia) being preferred suitable substituents in this instance also with the proviso, however, that the substitution may not involve only chlorine substituents);
$R^{2'}$ represents a straight-chain or branched alkyl group having 1 to 4 carbon atoms, or an aryl group which is optionally monosubstituted or polysubstituted by identical or different substituents and has 6 to 10 carbon atoms (the preferred aryl substituents already mentioned for $R^1$ in compounds of formula (Ia) being preferred suitable substituents);
$X''$ represents a hydrogen atom;
$A'$ represents a nitrogen atom, and
n is 0 or 1,
are also preferred for use according to the pesent invention.

Further preferred compounds for use according to the present invention are those of the general formula

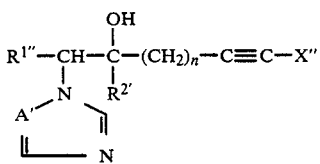

in which
R¹'' represents an aryloxy group which is monosubstituted or polysubstituted by chlorine and has 6 to 10 carbon atoms, and
R²', X'', A' and n have the meanings given above.

In each instance the use of the acid addition salts and metal salt complexes of the compounds of the formula (I) is also preferred.

Particularly preferred compounds of the formula (Ia) for use according to the present invention are those in which
R¹ represents a phenoxy or phenyl group which is optionally monosubstituted to trisubstituted by identical or different substituents selected from fluorine, chlorine, bromine, methyl, methoxy, nitro, trifluoromethyl, phenyl and chlorophenyl;
R² represents a tert-butyl group which is optionally monosubstituted or disubstituted by fluorine, chlorine or bromine, or a phenyl group which is optionally monosubstituted or trisubstituted by identical or different substituents selected from those mentioned immediately above under R¹;
X' represents a bromine or iodine atom, and also represents a hydrogen atom when R¹ does not simultaneously represent an optionally substituted phenoxy group, R² does not simultaneously represent a tert-butyl or optionally substituted phenyl group, and A does not simultaneously represent a nitrogen atom; and
A and n have the meanings given in the definition of compounds of formula (I).

Particularly preferred compounds of the formula (Ib) for use according to the present invention are those in which
R¹' represents a phenoxy group which is optionally monosubstituted to trisubstituted by identical or different substituents (the phenyl substituents already mentioned for R¹ in particularly preferred compounds of formula (Ia) being suitable substituents—with the proviso, however, that the substitution may not involve only chlorine substituents);
R²' represents a tert-butyl group, or a phenyl group which is optionally monosubstituted to trisubstituted by identical or different substituents (the phenyl substituents already mentioned for R¹ in particularly preferred compounds of formula (Ia) being suitable substituents); and
X'', A' and n have the meanings given above in the definition of compounds of formula (I)

Further particularly preferred compounds for use according to the present invention are those of the formula (Ic),
in which
R¹'' represents a phenoxy group which is monosubstituted or disubstituted by chlorine, and
R²', X'', A' and n have the meanings given above.

Active compounds, of the formula (I), to be used according to the invention are known (for compounds of the formula (Ic) and other known compounds of formula (I) see DE-OS (German Published Specification) No. 2,918,801).

According to the present invention we also provide, as new compounds, compounds of formulae (Ia) and (Ib), as defined above (especially the particularly preferred compounds of formulae (Ia) and (Ib) mentioned above).

The known compounds and novel compounds of the present invention can be obtained in a generally customary and known manner, by a process in which an azolyl ketone of the general formula

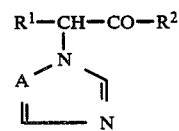

in which
A, R¹ and R² have the meanings given above,
(a) is reacted, in the case in which n is 0, with a mono-alkali metal salt or mono-Grignard compound of acetylene, in the presence of an aprotic organic solvent (such as tetrahydrofuran) at a temperature between 0° and 50° C., and the reaction mixture is then hydrolyzed, or
(b) is reacted, in the case in which n is 1, with a propargyl halide, in the presence of activated aluminium and in the presence of an aprotic organic solvent (such as tetrahydrofuran) at a temperature between −70° and +30° C., and, if appropriate, the compound obtained by the process (a) or (b), of the general formula

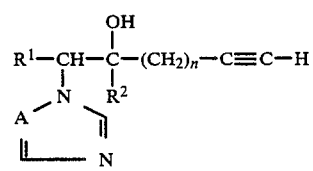

in which A, R¹, R² and n have the meanings given above, is reacted, in a customary manner, with bromine or iodine in the presence of a diluent (such as methanol) at a temperature between 0° and 50° C. (see also the Preparative Examples).

The diastereomer mixture may be separated in a customary manner, for example by fractional crystallization or by chromatographic separation methods.

The azolyl ketones of the formula (II) and their preparation have been known for a relatively long time (see, for example, DE-AS (German Published Specification) No. 2,105,490, U.S. Pat. No. 4,147,791, U.S. Application Ser. No. 291,699 filed Aug. 10, 1981, now pending, U.S. Pat. No. 4,255,434 and DE-OS (German Published Specification) No. 2,632,602).

The following acids are preferably used for the preparation of physiologically tolerated acid addition salts of the compounds of the formula (I): hydrohalic acids (such as hydrobromic acid and, preferably, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicyclic acid, sorbic acid and lactic acid) and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Preferred anions of the salts are those which are derived from the following acids: hydrohalic acids (such as hydrochloric acid and hydrobromic acid), phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compounds of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed fo combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, for example against the powdery mildew of barley or cereal causative organism (Erysiphe graminis), Sphaerotheca species, for example against the powdery mildew of cucumber causative organism (Sphaerotheca fuliginea), and Podosphaera species for example, against the powdery mildew of apple causative organism (Podosphaera leucotricha); and also for combating those fungi which cause rust diseases thus, for combating Puccinia species, for example against the brown rust of wheat causative organism (Puccinia recondita).

When used in appropriate concentrations, the substances according to the invention also exhibit a herbicidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold-mist and warm-mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl nephthalenes, chlorinated aromatic or chlorinated aliphatic hydrocarbons, such as chlorobenzenes, chloroethylenes are methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquid which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, generally amounts of active compound of 0.001 to 50 g per kilogram of seed, preferably 0.01 to 10 g, are generally required.

For the treatment of soil, generally acive compound concentrations of 0.00001 to 0.1% by weight, preferably 0.0001 to 0.02%, are required at the place of action.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

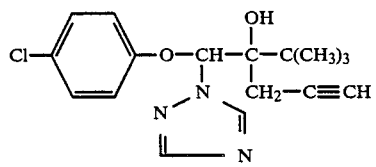

26 g (0.96 mol) of aluminum flakes were covered with a layer of 120 ml of tetrahydrofuran, and a few grains of iodine and a pinch of mercury (II) chloride were added. After 12 hours, a solution of 169 g (1.42 mol) of propargyl bromide in 170 ml of tetrahydrofuran was added dropwise at 60° C., while stirring vigorously. The mixture was then cooled to −60° C., and in the course of 2 hours, a solution of 293.8 g (1 mol) of 1-(4-chlorophenoxy)-3,3-dimethyl-1-(1H-1,2,4-triazol-1-yl)-butan-2-one in 330 ml of tetrahydrofuran was stirred in. 340 ml of a saturated ammonium chloride solution were then added to the reaction mixture at 0° C. The bulk of the solvent was distilled off under reduced pressure, and the residue was extracted with twice 600 ml of ethyl acetate. After the organic phase had been washed with water, it was dried over anhydrous sodium sulphate and then concentrated under reduced pressure. The precipitated crystalline product was filtered off and washed with isopropanol and diethyl ether. 131.1 g (39.3% of theory) of 4-(4-chlorophenoxy)-(1-H-1,2,4-triazol-1-yl)-methyl)-5,5-dimethyl-1-hexyn-4-ol of melting point 124° to 125° C. were obtained.

Example 2

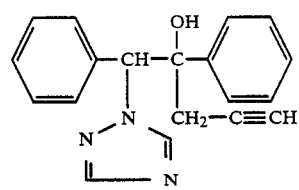

Analogously to Example 1, 8.8 g (33.3% of theory) of 4,5-diphenyl-5-(1H-1,2,4-triazol-1-yl)-pent-1-yn-4-ol were obtained as colorless crystals of melting point 119°–120° C., from 2.3 g (0.084 mol) of aluminum, 14.7 g (0.124 mol) of propargyl bromide and 23 g (0.087 mol) of ω-phenyl-ω-(1H-1,2,4-triazol-1-yl)-acetophenone in tetrahydrofuran.

Example 3

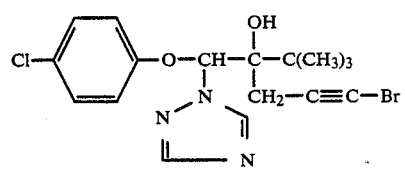

14 g (0.04 mol) of 4-((4-chlorophenoxy)-(1H-1,2,4-triazol-1-yl)-methyl)-5,5-dimethyl-hex-1-yn-4-ol (obtained as described in Example 1), dissolved in 75 ml of dioxane, were added dropwise to a solution of 7.7 g (0.048 mol) of bromine in 40 ml of 10% strength sodium hydroxide solution at 0° C. After five hours, the reaction mixture was stirred into ice water. The precipitated product was filtered off under suction, washed with water and dried. 14.2 g (86.1% of theory) of 1-bromo-4-((4-chlorophenoxy)-(1H-1,2,4-triazol-1-yl)-methyl)-5,5-dimethyl-hex-1-yn-4-ol of melting point 156° to 160° C. were obtained.

Example 4

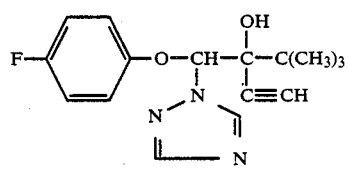

Product 4: Diastereomer mixture
Product 5: Form A (one of the two possible geometrical isomers)

Acetylene was passed into a suspension of 31.4 g (0.28 mol) of potassium tert-butylate in 300 ml of tetrahydrofuran for 30 minutes at 15° C., while stirring. A solution of 55.5 g (0.2 mol) of 1-(4-fluorophenoxy)-3,3-dimethyl-1-(1H-1,2,4-triazol-1-yl)-butan-2-one in 150 ml of tetrahydrofuran was then added dropwise in the course of one hour, while acetylene was further passed through the mixture. After a further two hours, the solution was adjusted to a pH value of 8 by the addition of 175 ml of a 23% strength aqueous ammonium chloride solution. The mixture was extracted with twice 200 ml of ethyl acetate, the extracts were washed with water, and the solution was concentrated under reduced pressure. The remaining solid residue was triturated with petroleum ether. 27.2 g (44.8% of theory) of 3-((4-fluorophenoxy)-(1H-1,2,4-triazol-1-yl)-methyl)-4,4-dimethyl-pent-1-yn-3-ol of melting point 155° to 161° C. were thus obtained. By cooling and triturating, a further 3.2 g (5.3% of theory) of a pure diastereomeric form A of melting point 134° to 135° C. were obtained from the petroleum ether phase.

Example 5

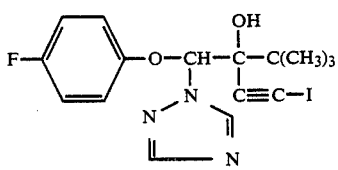
(6)

12.5 g (0.049 mol) of iodine were introduced in portions into a solution of 14.7 g (0.049 mol) of 3-((4-fluorophenoxy)-(1H-1,2,4-triazol-1-yl)-methyl)-4,4-dimethyl-pent-1-yn-3-ol (obtained as described in Example 4) in 250 ml of methanol at 20° to 25° C., while stirring, and 20 ml of concentrated sodium hydroxide solution were added dropwise at the same time. After 12 hours, the solution was filtered and the filtrate was stirred into 500 ml of water. The precipitated semi-solid product was taken up in ethyl acetate. The solution was washed with water and, after it had been dried over anhydrous sodium sulphate, was concentrated by evaporation under reduced pressure. The resinous residue was dissolved in a small quantity of diethyl ether, and petroleum ether was added to the solution. The product which had crystallized out was filtered off and washed with petroleum ether. 15.1 g (71.9% of theory) of 1-iodo-3-((4-fluorophenoxy)-(1H-1,2,4-triazol-1-yl))-methyl-4,4-dimethyl-pent-1-yn-3-ol were obtained as colorless crystals of melting point 140° to 149° C.

The compounds which follow, of the general formula

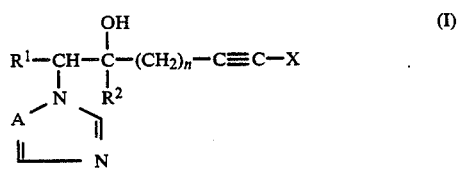
(I)

were obtained in a corresponding manner:

TABLE 1

| Compound No. | $R^1$ | $R^2$ | A | n | X | Melting point (°C.) |
|---|---|---|---|---|---|---|
| 7 | Cl—⟨⟩—O— | —C(CH$_3$)$_3$ | N | 0 | H | 153–55 (A-Form)* |
| 8 | Cl—⟨⟩—O— | —C(CH$_3$)$_3$ | N | 0 | H | 133–43 |
| 9 | Cl,Cl—⟨⟩—O— | —C(CH$_3$)$_3$ | N | 0 | H | 163–66 (A-Form)* |
| 10 | ⟨⟩—⟨⟩—O— | —C(CH$_3$)$_3$ | N | 0 | H | 187–89 |
| 11 | ⟨⟩—O— | —C(CH$_3$)$_3$ | N | 0 | H | 191–93 |
| 12 | ⟨⟩—⟨⟩—O— | —C(CH$_3$)$_3$ | N | 0 | I | 148–53 |
| 13 | Cl,Cl—⟨⟩—O— | —C(CH$_3$)$_3$ | N | 1 | H | resin |
| 14 | Cl—⟨⟩—O— | ⟨⟩ | N | 1 | H | 157–58 |
| 15 | Cl—⟨⟩—⟨⟩Cl—O— | —C(CH$_3$)$_3$ | N | 1 | H | resin |
| 16 | Br—⟨⟩—O— | —C(CH$_3$)$_2$CH$_2$Br | N | 1 | H | 127 |
| 17 | Cl—⟨⟩—O— | —C(CH$_3$)$_3$ | N | 1 | I | 2ol |

TABLE 1-continued

| Compound No. | R¹ | R² | A | n | X | Melting point (°C.) |
|---|---|---|---|---|---|---|
| 18 | 2,4-dichloro-phenoxy | —C(CH₃)₃ | N | 1 | I | 176–77 |
| 19 | 4-chloro-phenoxy | phenyl | N | 1 | I | 171–72 |
| 20 | 3-chloro-4-(4-chlorophenyl)phenoxy | —C(CH₃)₃ | N | 1 | I | 156–58 |
| 21 | 4-bromo-phenoxy | —C(CH₃)₂CH₂Br | N | 1 | I | 194–95 |
| 22 | 4-chlorophenyl | 4-chlorophenyl | N | 1 | I | 157–58 |
| 23 | 4-chlorophenyl | 4-chlorophenyl | N | 1 | H | 176–77 |
| 24 | 4-chloro-phenoxy | —C(CH₃)₃ | CH | 0 | H | 188–28 |
| 25 | 4-chloro-phenoxy | —C(CH₃)₃ | CH | 0 | H | 143–44 (B-Form)* |
| 26 | 2-chloro-phenoxy | —C(CH₃)₃ | CH | 0 | H | resin |
| 27 | 4-chloro-phenoxy | —C(CH₃)₃ | CH | 0 | I | 80–105 |
| 28 | 4-fluoro-phenoxy | —C(CH₃)₃ | N | 0 | H | 160–68 (B-Form)* |

*A Form and B Form: the two possible geometrical isomers

The fungicidal activity of the compounds of this invention is illustrated by the following biotest-examples.

In these examples, the compounds according to the present invention are each identified by the number (given in brackets) of the corresponding preparative example.

The known comparison compounds are identified as follows:

(A)

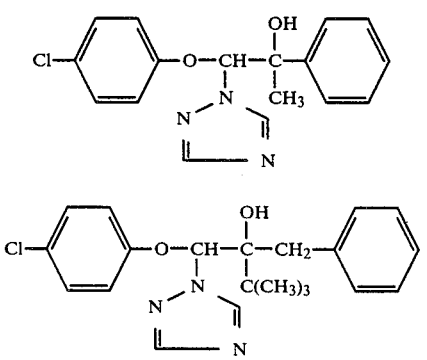
(B)

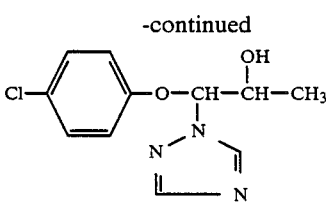
(C)

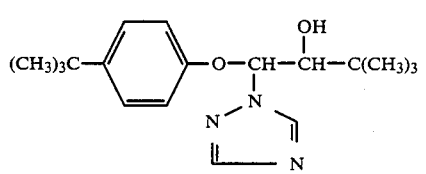
(D)

Example 6

Sphaerotheca test (cucumber) /protective/
Solvent: 4.7 parts by weight of acetone
Emulsifier: 0.3 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were dusted with conidia of the fungus Sphaerotheca fuliginea.

The plants were then placed in a greenhouse at 23° to 24° C. and at a relative atmospheric humidity of about 75%.

Evaluation was carried out 10 days after the inoculation.

In this test, a clearly superior activity compared with the prior art was shown, for example, by the compounds (8), (7) and (1).

TABLE 2

Sphaerotheca test (cucumber)/protective/

| Active compound | | Infestation in % at an active compound concentration of 0.0001% |
|---|---|---|
| 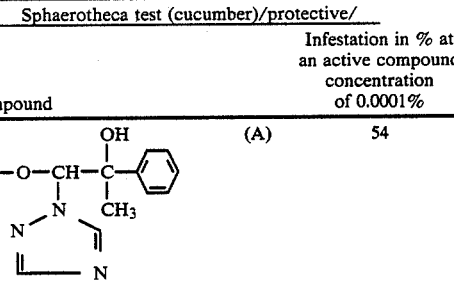 (known) | (A) | 54 |
| 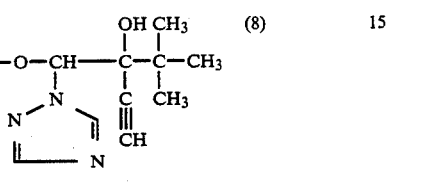 | (8) | 15 |
| 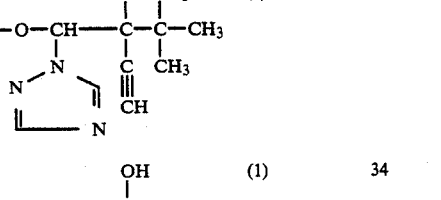 | (7) | 29 |
| 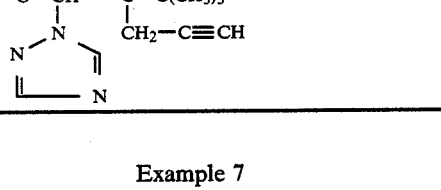 | (1) | 34 |

Example 7

Podosphaera test (apple) /protective/
Solvent: 4.7 parts by weight of acetone
Emulsifier: 0.3 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated by dusting with conidia of the powdery mildew of apple causative organism (Podosphaera leucotricha).

The plants were then placed in a greenhouse at 23° C. and a relative atmospheric humidity of about 70%.

Evaluation was carried out 9 days after the inoculation.

In this test, a clearly superior activity compared with the prior art was shown, for example, by the compounds (5), (8), (7), (1) and (16).

TABLE 3

Podosphaera test (apple)/protective/

| Active compound | | Infestation in % at an active compound concentration of 0.001% |
|---|---|---|
| 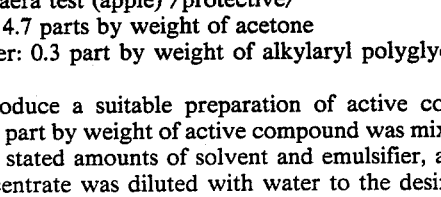 (known) | (B) | 14 |
| 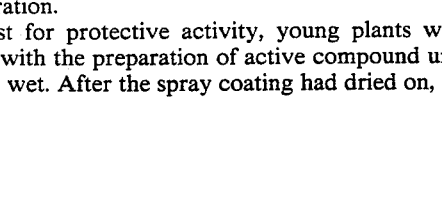 (A-Form) | (5) | 0 |
|  | (8) | 1 |
| 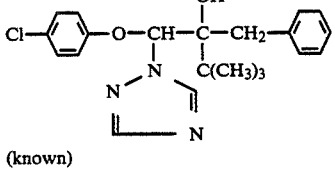 (A-Form) | (7) | 6 |
| 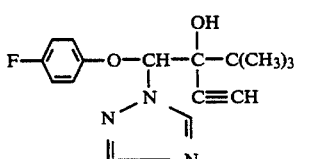 | (1) | 0 |
| 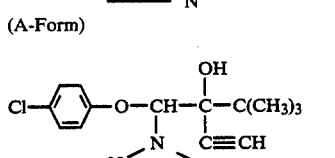 | (16) | 4 |

Example 8

Erysiphe test (barley) /protective/
Solvent: 100 parts by weight of dimethylformamide Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f. sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (4), (5), (8), (7), (10), (1), (13), (14), (16) and (3).

TABLE 4

Erysiphe test (barley)/protective/

| Active compound | | Active compound concentration in the spray liquor in % by weight | Disease infestation in % of the untreated control |
|---|---|---|---|
| 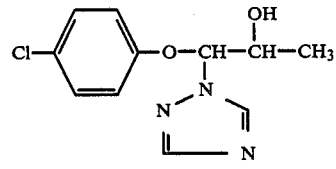 (known) | (C) | 0.0025 | 100 |
| 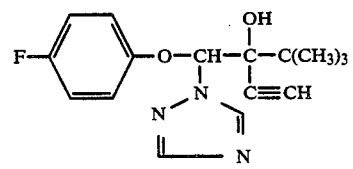 | (4) | 0.0025 | 15.0 |
| 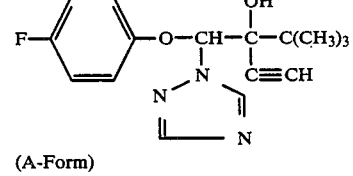 (A-Form) | (5) | 0.0025 | 12.5 |
| 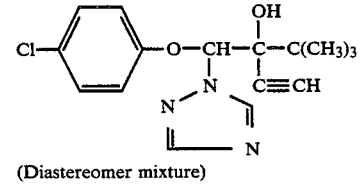 (Diastereomer mixture) | (8) | 0.0025 | 0.0 |
| 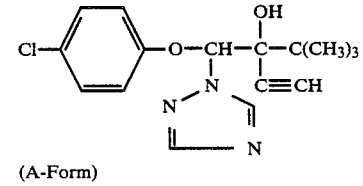 (A-Form) | (7) | 0.0025 | 0.0 |
| 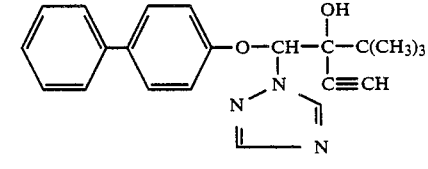 | (10) | 0.0025 | 16.3 |

TABLE 4-continued

Erysiphe test (barley)/protective/

| Active compound | | Active compound concentration in the spray liquor in % by weight | Disease infestation in % of the untreated control |
|---|---|---|---|
| 4-Cl-C₆H₄-O-CH(N-N=CH-N=N triazole)-C(OH)(C(CH₃)₃)(CH₂-C≡CH) | (1) | 0.0025 | 0.0 |
| 2,4-Cl₂-C₆H₃-O-CH(N-N=CH-N=N triazole)-C(OH)(C(CH₃)₃)(CH₂-C≡CH) | (13) | 0.0025 | 0.0 |
| 4-Cl-C₆H₄-O-CH(N-N=CH-N=N triazole)-C(OH)(C₆H₅)(CH₂-C≡CH) | (14) | 0.0025 | 12.5 |
| 4-Br-C₆H₄-O-CH(N-N=CH-N=N triazole)-C(OH)(CH₂-C≡CH)-C(CH₃)₂-CH₂Br | (16) | 0.0025 | 8.8 |
| 4-Cl-C₆H₄-O-CH(N-N=CH-N=N triazole)-C(OH)(C(CH₃)₃)(CH₂-C≡CBr) | (3) | 0.0025 | 8.8 |

Example 9

Erysiphe test (barley) /seed treatment

The active compounds were used as dry dressings. These were prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of Erysiphe graminis f. sp. hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art was shown, for example, by the compounds (4), (5), (8) (7), (1) and (14).

TABLE 5

Erysiphe test (barley)/seed treatment

| Active compound | | Amount of active compound applied in mg/kg of seed | Disease infestation in % of the untreated control |
|---|---|---|---|
| 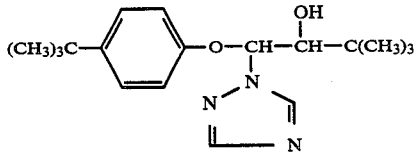 (known) | (D) | 2500 | 100 |
| 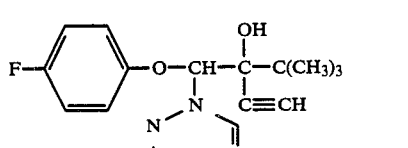 | (4) | 1000 | 0.0 |
| 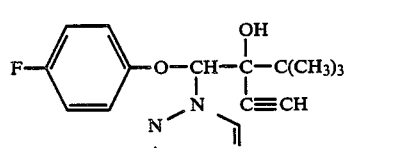 (A-Form) | (5) | 1000 | 0.0 |
| 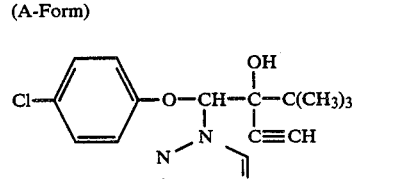 | (8) | 2500 | 0.0 |
| 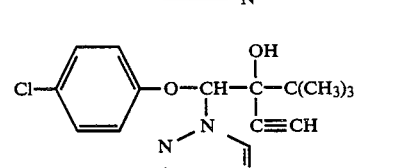 (A-Form) | (7) | 2500 | 0.0 |
| 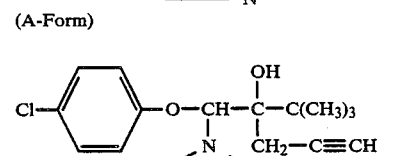 | (1) | 1000 | 0.0 |
| 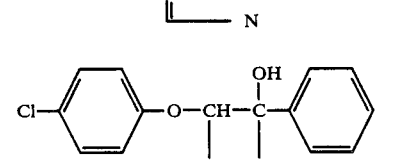 | (14) | 1000 | 16.3 |

Example 10

Puccinia test (wheat) /protective/
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were inoculated with a spore suspension of Puccinia recondita in a 0.1% strength aqueous agar solution. After the spore suspension had dried on, the plants were sprayed with the preparation of active compound until dew-moist. The plants remained in an incubation cabin at 20° C. and 100% relative atmospheric humidity for 24 hours.

The plants were placed in a greenhouse at a temperature of about 20° C. and a relative atmospheric humidity of about 80% in order to promote the development of rust pustules.

Evaluation was carried out 10 days after the inoculation.

In this test, a clearly superior activity compared with the prior art was shown, for example, by the compounds (8), (1), (13) and (3).

TABLE 6

Puccinia test (wheat)/protective/

| Active compound | | Active compound concentration in the spray liquor in % by weight | Disease infestation in % of the untreated control |
|---|---|---|---|
| 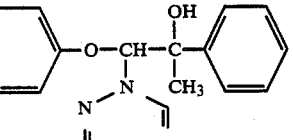 | (A) | 0.025 | 100 |
| 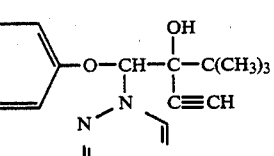 | (8) | 0.025 | 12.5 |
| 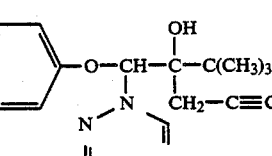 | (1) | 0.025 | 8.8 |
| 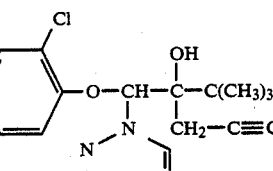 | (13) | 0.025 | 12.5 |
| 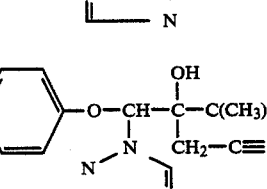 | (3) | 0.025 | 0.0 |

It will be appreciated that the instant specification and examples are set forth by way of illustration and not limitation, and that various modifications and changes may be made without departing from the spirit and scope of the present invention.

We claim:

1. A method of combating fungi which comprises applying to the fungi, or to a habitat thereof, a fungicidally effective amount of an alkinyl-azole derivative of the formula

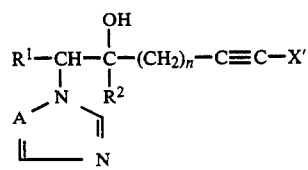

in which
A is a nitrogen atom or the CH group,
$R^1$ is an aryloxy group,
$R^2$ is an alkyl group having 1 to 4 carbon atoms which is optionally substituted by halogen, or an aryl group,
the aryl or aryloxy groups of $R^1$ and $R^2$ being phenyl or naphthyl optionally substituted by halogen, alkyl having 1 to 4 carbon atoms, nitro, halogenoalkyl having 1 or 2 carbon atoms and 1 to 5 identical or different halogen atoms, or phenyl which is optionally substituted by halogen, X' is a hydrogen, bromine or iodine atom, and n is 0 or 1, or an acid addition salt or metal salt complex thereof.

2. A method according to claim 1, in which $R^2$ is an alkyl group having 1 to 4 carbon atoms, a tert.-butyl group which is substituted by halogen, or a phenyl or naphthyl group which is optionally substituted by halogen, alkyl having 1 to 4 carbon atoms, alkoxy having 1 to 4 carbon atoms, nitro, halogenoalkyl having 1 or 2 carbon atoms and 1 to 5 identical or different halogen atoms, or phenyl which is optionally substituted by halogen, and X' is a bromine or iodine atom, or also may be a hydrogen atom when A is not simultaneously a nitrogen atom.

3. A method according to claim 1 in which $R^1$ is a phenoxy group which is optionally monosubstituted to trisubstituted by substituents selected from fluorine, chlorine, bromine, methyl, methoxy, nitro, trifluoromethyl, phenyl and chlorophenyl;

$R^2$ is a tert-butyl group which is optionally monosubstituted or disubstituted by fluorine, chlorine or bromine, or a phenyl group which is optionally monosubstituted to trisubstituted by substituents selected from fluorine, chlorine, bromine, methyl, methoxy, nitro, trifluoromethyl, phenyl and chlorophenyl; and X' is a bromine or iodine atom, or also may be a hydrogen atom when $R^2$ is not simultaneously a tert-butyl or optionally substituted phenyl group and A is not simultaneously a nitrogen atom.

4. A method according to claim 1, in which $R^1$ is an unsubstituted phenoxy or naphthyloxy group or a phenoxy or naphthyloxy group which carries at least one substituent other than or in addition to chlorine, X' is a hydrogen atom, and A is a nitrogen atom.

5. A method according to claim 4, in which $R^1$ is a phenoxy group which is optionally substituted by up to three substituents each independently selected from the group consisting of fluorine, chlorine, bromine, methyl, methoxy, nitro, trifluoromethyl, phenyl and chlorophenyl, and $R^2$ is a tert-butyl group, or a phenyl group which is substituted by up to three substituents each independently selected from the group consisting of fluorine, chlorine, bromine, methyl, methoxy, nitro, trifluoromethyl, phenyl and chlorophenyl.

6. A method according to claim 1, in which $R^1$ is a phenoxy or naphthyloxy group which is substituted by chlorine.

7. A method according to claim 1, in which $R^1$ is a monochloro- or dichloro-phenoxy group.

8. A method according to claim 1, wherein the fungicidally active compound is 4-((4-chlorophenoxy)-(1H-1,2,4-triazol-1-yl)-methyl)-5,5-dimethyl-1-hexyn-4-ol.

9. A method according to claim 1, wherein the fungicidally active compound is 1-bromo-4-((4-chlorophenoxy)-(1H-1,2,4-triazol-1-yl)-methyl)-5,5-dimethyl-hex-1-yn-4-ol.

10. A method according to claim 1, wherein the fungicidally active compound is 3-((4-fluorophenoxy)-(1H-1,2,4-triazol-1-yl)-methyl)-4,4-dimethyl-pent-1-yn-3-ol.

11. A method according to claim 1, wherein the fungicidally active compound is 3-((4-chlorophenoxy-(1H-1,2,4-triazol-1-yl)-methyl)-4,4-dimethyl-pent-1-yn-3-ol.

12. A method of combating fungi which comprises applying to the fungi, or to a habitat thereof, a fungicidally effective amount of an alkinyl-azole derivative of the formula

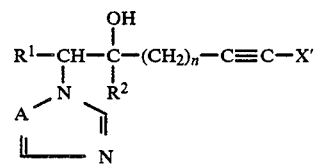

in which

A is a nitrogen atom or the CH group, $R^1$ is an aryl group, $R^2$ is an alkyl group having 1 to 4 carbon atoms which is optionally substituted by halogen, or an aryl group, the aryl groups of $R^1$ and $R^2$ being phenyl or naphthyl optionally substituted by halogen, alkyl having 1 to 4 carbon atoms, alkoxy having 1 to 4 carbon atoms, nitro, halogenoalkyl having 1 or 2 carbon atoms and 1 to 5 identical or different halogen atoms, or phenyl which is optionally substituted by halogen, X' is a bromine or iodine atom, and n is 0 or 1, or an acid addition salt or metal salt complex thereof.

13. A method according to claim 12, in which $R^2$ is an alkyl group having 1 to 4 carbon atoms, a tert.-butyl group which is substituted by halogen, or a phenyl or naphthyl group which is optionally substituted by halogen, alkyl having 1 to 4 carbon atoms, alkoxy having 1 to 4 carbon atoms, nitro, halogenoalkyl having 1 or 2 carbon atoms and 1 to 5 identical or different halogen atoms, or phenyl which is optionally substituted by halogen.

14. A method according to claim 12, in which $R^1$ is a phenoxy group which is optionally monosubstituted to trisubstituted by substituents selected from fluorine, chlorine, bromine, methyl, methoxy, nitro, trifluoromethyl, phenyl and chlorophenyl; and $R^2$ is a tert-butyl group which is optionally monosubstituted or disubstituted by fluorine, chlorine or bromine, or a phenyl group which is optionally monosubstituted to trisubstituted by substitutents selected from fluorine, chlorine, bromine, methyl, methoxy, nitro, trifluoromethyl, phenyl and chlorophenyl.

15. A method according to claim 12, wherein the substituents on the aryl group of $R^1$ and $R^2$ are selected from halogen, alkyl having 1 to 4 carbon atoms, alkoxy having 1 to 4 carbon atoms, nitro, halogenoalkyl having 1 or 2 carbon atoms and 1 to 5 identical or different halogen atoms, and phenyl which is optionally substituted by halogen.

* * * * *